United States Patent [19]

Hadary

[11] 4,397,327
[45] Aug. 9, 1983

[54] TOOTHPICK HOLDER

[76] Inventor: Joseph Hadary, 5405 Linden Ct., Bethesda, Md. 20014

[21] Appl. No.: 206,710

[22] Filed: Nov. 14, 1980

[51] Int. Cl.³ .............................................. A61C 15/00
[52] U.S. Cl. ......................................... 132/89; 132/90
[58] Field of Search ............................ 132/89, 90, 93; 433/147

[56] References Cited

U.S. PATENT DOCUMENTS

| 736,101 | 8/1903 | Hough | 433/147 |
|---|---|---|---|
| 792,471 | 6/1905 | Smith | 132/89 UX |
| 797,684 | 8/1905 | Harper | 433/147 |
| 3,660,902 | 5/1972 | Axelsson | 132/89 |
| 4,033,007 | 7/1977 | Hadary | 132/90 |

Primary Examiner—G. E. McNeill
Attorney, Agent, or Firm—Dennis H. Lambert

[57] ABSTRACT

A toothpick holder for holding a toothpick in any one of several adjusted positions for facilitating access to difficult to reach areas of the mouth, includes a handle with a toothpick retainer projecting perpendicularly therefrom, with aligned openings in the retainer for snugly receiving a toothpick. The retainer is held latched in position relative to the handle by a releasable latch, which can be manipulated to release the retainer either for removal from the handle or adjustment to a different position relative thereto. The openings in the retainer are of different size and are configured to snugly receive at both openings spaced portions of a toothpick. Further, the holder of the invention is specifically designed to properly orient a toothpick having a wedge shaped cross section for optimum cleaning of the space between the teeth.

8 Claims, 7 Drawing Figures

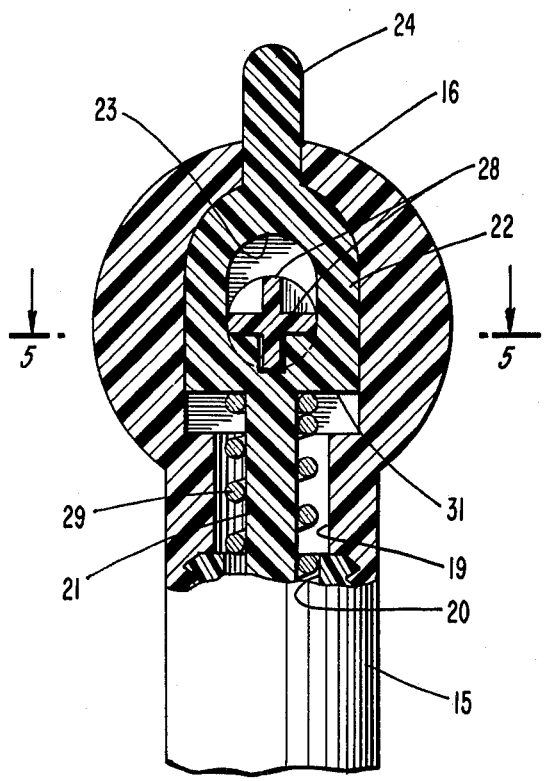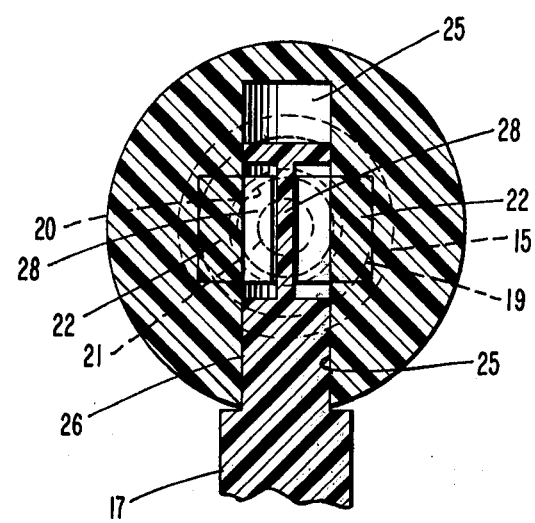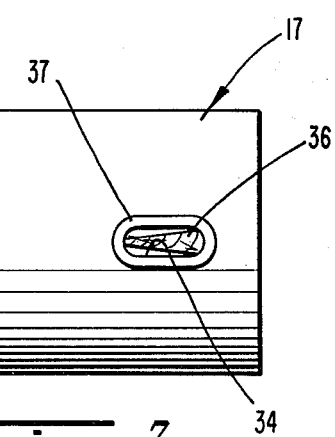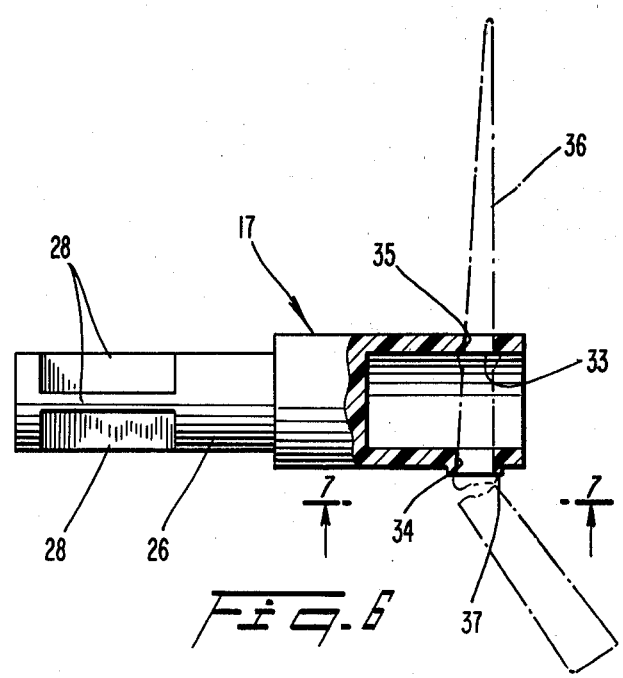

TOOTHPICK HOLDER

BACKGROUND OF THE INVENTION

1. Field of the Invention

This invention relates to dental implements, and more particularly, to a toothpick holder for holding a toothpick in any one of several different adjusted positions for easier access to difficult to reach areas of the mouth.

More specifically, the present invention relates to a toothpick holder which includes a handle with a toothpick retainer projecting perpendicularly therefrom and rotatable about its axis to several different latched positions. The retainer has a pair of aligned openings therein for snugly receiving a toothpick of yieldable material, whereby the toothpick is held in a firmly latched position with its axis extending in a desired direction relative to the axis of the handle. By manipulating a latch member, the retainer may be released for removal from the handle or adjustment to different latched positions.

It is well known by the dental profession that brushing does not always adequately clean the teeth, particularly in the areas between the teeth. Thus, flossing and other cleaning methods are recommended in conjunction with brushing. Moreover, the proper use of toothpicks is very beneficial in any oral hygiene program, and can be particularly effective in cleaning the spaces between the teeth.

However, except for a few attempts at developing a toothpick holder, people are generally limited to the use of wood or plastic toothpicks held in the users hand. Accordingly, the use of a toothpick is only partially effective in cleaning the teeth, and those areas which are difficult to reach are usually not cleaned.

Prior Art

Examples of prior art toothpick holders are shown in U.S. Pat. Nos. 710,498, 1,291,282 and 3,892,040. In U.S. Pat. No. 710,498 a quill-like member is inserted through a shaped holder whereupon the quill-like member is curved to form a pick. U.S. Pat. No. 1,291,282 discloses a threaded holder having a pair of openings therein for receiving a toothpick in either of two different positions. U.S. Pat. No. 3,892,040 discloses a holder having a threaded sleeve which is movable against a round toothpick to clamp the toothpick in position.

U.S. Pat. No. 3,471,929 discloses a dental implement in which a shaft 26 is held to a handle by a pin 8. A blade 30 is carried by the shaft for performing gum cutting operations.

None of the above patents teaches a toothpick holder capable of holding a toothpick with a wedge shaped cross section in any one of several different adjusted latched positions, and with the particular cooperation between the elements and pick as set forth more fully hereinafter, wherein the holder properly orients such a wedge shaped toothpick for optimum effectiveness in all areas of the mouth.

SUMMARY OF THE INVENTION

Therefore, it is an object of the present invention to provide a toothpick holder which holds a toothpick in any of several positions to facilitate access to difficult to reach areas of the mouth.

Another object of the invention is to provide a toothpick holder which holds a toothpick in several latched positions whereby the pick is positively held for secure use to clean the teeth in even difficult to reach areas of the mouth.

A further object of the invention is to provide a toothpick holder in which the toothpick is made of relatively soft, yieldable material and the holder has a pair of aligned openings therethrough in which the toothpick is snugly received at spaced points on the toothpick, the toothpick yielding at those points to deform slightly whereby the toothpick is securely held in position.

BRIEF DESCRIPTION OF THE DRAWINGS

FIG. 4 is an enlarged, fragmentary sectional view of the toothpick holder of FIG. 1, taken along line 4—4 in FIG. 3;

FIG. 5 is a transverse sectional view taken along line 5—5 in FIG. 4;

FIG. 6 is an enlarged, fragmentary sectional view of the toothpick retainer, showing the manner in which a toothpick is held thereby; and FIG. 7 is an enlarged, fragmentary sectional view taken along the line 7—7 in FIG. 6.

DETAILED DESCRIPTION OF THE PREFERRED EMBODIMENT

Figure 1:
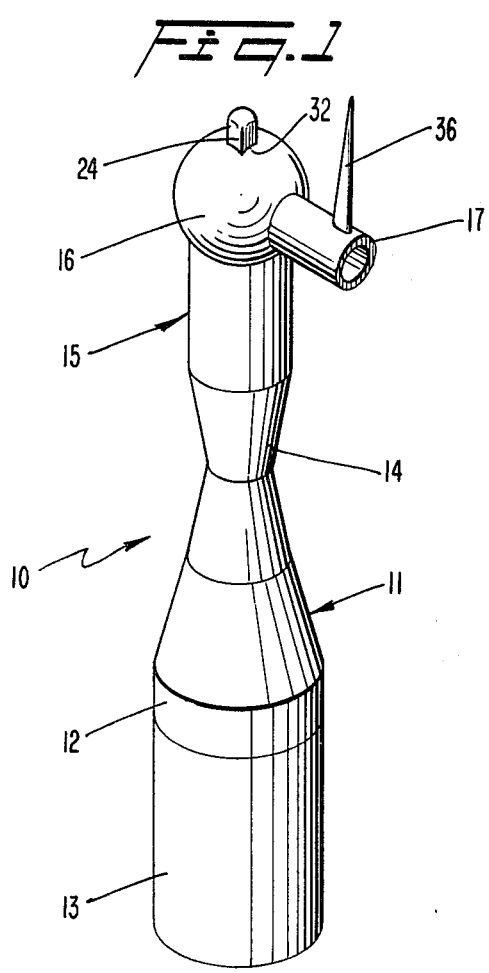
FIG. 1 is a perspective view of a toothpick holder in accordance with the invention, showing a toothpick in one of the adjusted positions.

In the drawings, wherein like reference numerals indicate like parts throughout the several views, the toothpick holder of the invention is referred to generally at 10 in FIG. 1 and comprises a handle 11 having an enlarged base 12 with a removable cap 13 which defines a hollow interior space (not shown) in which spare picks and the like may be stored. The base 12 tapers inwardly toward its upper end to a generally hour-glass shaped portion 14 which facilitates gripping by the user. At the upper end of the hour-glass shaped portion, a cylindrical head member 15 projects axially from the end of the handle and has a rounded end 16 thereon for releasably holding the toothpick retainer 17.

Figure 3:
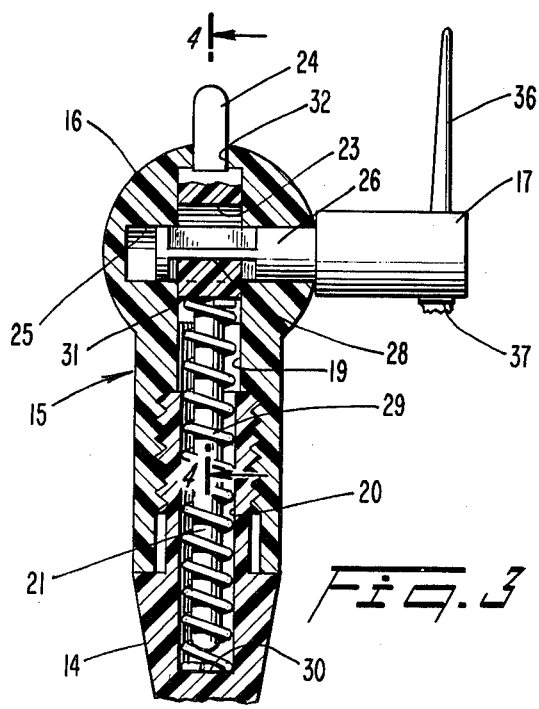
FIG. 3 is an enlarged, fragmentary sectional view of the toothpick holder of FIG. 1.
Figure 2:
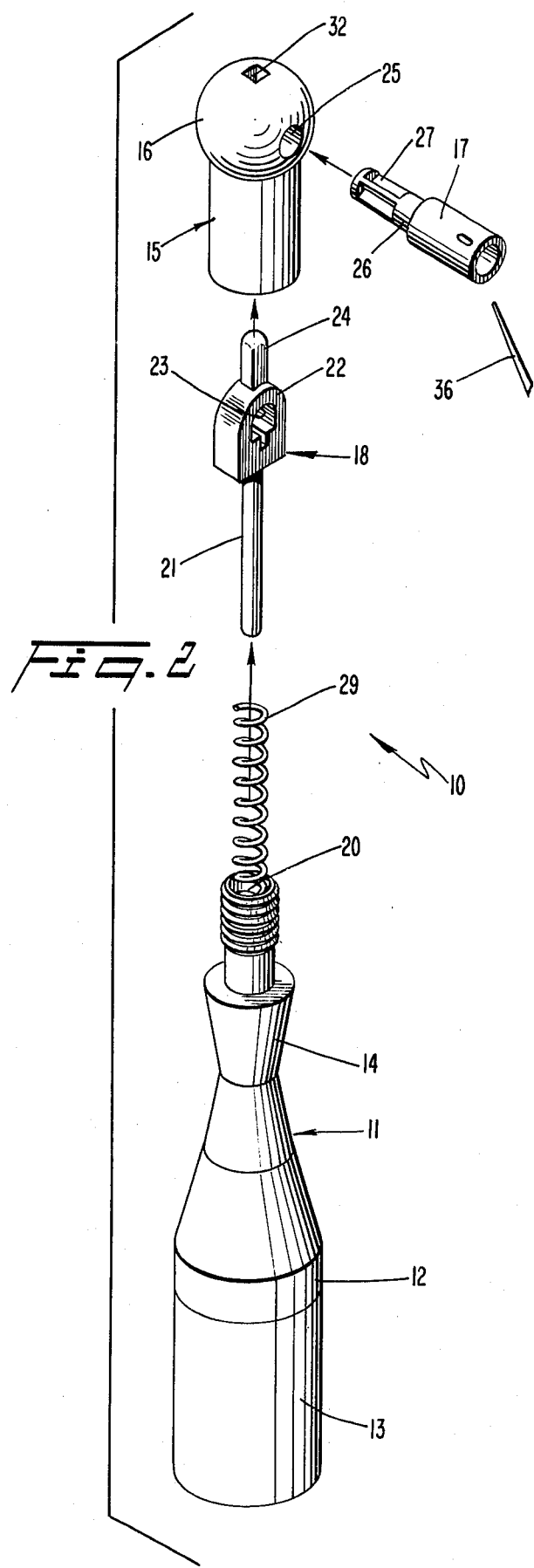
FIG. 2 is an exploded perspective view of the toothpick holder of FIG. 1.

As seen best in FIGS. 2, 3 and 4, a manually operable latch 18 is reciprocable in the hollow interior 19 of the head member 15 and the hollow interior 20 of the upper end of handle 14. The latch 18 has a depending cylindrical stem 21 and a latching portion 22 with a key-hole shaped latching opening 23 therethrough and a manually engageable actuating pin 24 projecting upwardly therefrom.

The head member 15 has a transverse bore 25 therethrough which intersects the upper end of hollow interior 19 of the head member 15. The bore 25 opens through one side only of the head member, and the pick retainer 17 has a reduced diameter end 26 which is received in this bore.

The midportion 27 of the reduced diameter end 26 is cross-shaped in cross section at 28 to define several latching projections which cooperate with the latching opening 23 in the latching member 18 to positively latch the toothpick retainer 17 in any one of four adjusted positions. A spring 29 is disposed around the stem 21 within the bores 19 and 20 and is normally engaged between the bottom 30 of bore 20 and a shoulder 31 on the underside of latching member 18 to urge the latching member upwardly into latching engagement with the cross-shaped portion 28 of toothpick retainer 17. In this position of the latching member, the actuating pin 24 projects through opening 32 in the top of rounded portion 16 of head member 15. Thus, the user of the toothpick holder of the invention may depress the pin 24 to release the latching member from the toothpick retainer for rotation of the retainer to a different adjusted position or to completely release the retainer from the handle.

The toothpick retainer 17 has a blind bore 33 extending inwardly from the outer end thereof and a pair of aligned openings 34 and 35 are formed on diametrically opposite sides of the retainer for receiving a toothpick 36. The openings 34 and 35 are of different size, with the opening 34 being larger than opening 35, and the edges of openings 34 and 35 closest to the outer end of retainer 17 are spaced the same distance from the outer end of retainer 17. Moreover, the slot or opening 34 has any suitable identifying means associated therewith, such as rib 37, so that quick identification can be made of the proper opening into which the toothpick should be first inserted to achieve the orientation shown in the drawings.

The openings are elongate, uniformly shaped slots to snugly receive and grip a toothpick 36, so that when a toothpick 36 is inserted through openings 34 and 35, the wedge shaped cross section of the toothpick is snugly received in both openings, and in fact, the material of the toothpick actually swells or bulges around the edges of the openings. An example of a suitable toothpick is available under the trademark "stim-u-dent" by Johnson & Johnson and is made of balsa wood. After the toothpick is fully inserted into the openings 34 and 35, the unused portion projecting rearwardly of the retainer is broken off as indicated in FIG. 6. It should be noted that the wedge-shaped cross section of the toothpick is desired, as is the use of a soft material such as balsa. See, for example, U.S. Pat. No. 2,008,206.

The toothpick holder may be made of plastic or any other suitable material, and toothpicks other than that specifically mentioned above may be used.

As this invention may be embodied in several forms without departing from the spirit or essential characteristics thereof, the present embodiment is, therefore, illustrative and not restrictive, since the scope of the invention is defined by the appended claims rather than by the description preceeding them, and all changes that fall within the metes and bounds of the claims or that form their functional as well as conjointly cooperative equivalents are, therefore, intended to be embraced by those claims.

What I claim as new and desire to secure by Letters Patent of the United States is:

1. A toothpick holder for holding a toothpick in any one of a plurality of positively latched adjusted positions, comprising:
    an elongate handle having an enlarged base on one end thereof and a head member on the other end; said head member having a transverse bore therein;
    an elongate toothpick retainer projecting from the bore in the head member with its axis extending in a direction substantially perpendicular to the axis of the handle and having a transverse opening therein for snugly engaging a toothpick at spaced locations on the toothpick and holding the toothpick with the axis of the toothpick at substantially a right angle to the axis of the retainer, the opening in the retainer being disposed in offset, spaced relation to the axis of the handle whereby the toothpick is held in spaced, offset relation to the handle;
    latching means for cooperative engagement with complemental latching means on the retainer to releasably latch the retainer in any one of several adjusted positions of rotation about the retainer axis, to thereby latch the toothpick in any one of several adjusted orientations relative to the handle; and
    actuator means to selectively release the latching means.

2. A toothpick holder as in claim 1, wherein:
    the retainer has an axially extending bore therein; and
    the opening intersects the axially extending bore, whereby a pair of openings are defined, aligned with one another on diametrically opposite sides of the retainer and communicating with the bore.

3. A toothpick holder as in claim 2, wherein:
    the openings are of different size and are slot-shaped in cross-section.

4. A toothpick holder as in claim 1 or 2, wherein:
    the latching means includes a latching member reciprocable in the head member; and
    spring means is carried by the handle for yieldably urging the latching member into latching relationship with the retainer.

5. A toothpick holder as in claim 4, wherein:
    the retainer has a portion received in the bore in the head member and a part of said portion is cross-shaped in cross section; and
    said latching member has a shaped opening therein through which said retainer portion extends, said shaped opening including a part shaped for latching engagement with the cross-shaped section.

6. A toothpick holder as in claim 1, wherein:
    the latching means is carried by the head member; and
    said actuator means comprises a manually engageable actuator pin projecting from the head member and connected with the latching means.

7. A toothpick holder as in claim 6, wherein:
    the latching means includes a latching member reciprocable in the head member; and
    spring means is carried by the handle for yieldably urging the latching member into latching relationship with the retainer.

8. A toothpick holder as in claim 1, wherein:
    the toothpick has a wedge shape in transverse cross-section; and
    the toothpick is made of balsa wood.

* * * * *